(12) United States Patent
Lapoujade et al.

(10) Patent No.: US 8,097,086 B2
(45) Date of Patent: Jan. 17, 2012

(54) METHOD AND EQUIPMENT FOR PRODUCING FRUIT SUGAR SYRUPS HAVING HIGH FRUCTOSE CONTENT

(75) Inventors: Pierre Lapoujade, Castelsarrasin (FR); Alain Guibert, Escalquens (FR); Francoise Ouarne, Castanet Tolosan (FR)

(73) Assignees: Nutritis, Montauban (FR); Institut National des Sciences Appliquees Toulouse, Toulouse (FR)

( * ) Notice: Subject to any disclaimer, the term of this patent is extended or adjusted under 35 U.S.C. 154(b) by 268 days.

(21) Appl. No.: 12/524,956

(22) PCT Filed: Jan. 24, 2008

(86) PCT No.: PCT/FR2008/000085
§ 371 (c)(1),
(2), (4) Date: Jul. 29, 2009

(87) PCT Pub. No.: WO2008/107560
PCT Pub. Date: Sep. 12, 2008

(65) Prior Publication Data
US 2010/0006091 A1    Jan. 14, 2010

(30) Foreign Application Priority Data
Feb. 1, 2007 (FR) ..................... 07 00712

(51) Int. Cl.
| | |
|---|---|
| *C13K 1/08* | (2006.01) |
| *C13K 13/00* | (2006.01) |
| *C13B 35/06* | (2011.01) |
| *C13B 20/00* | (2011.01) |
| *C13B 20/12* | (2011.01) |
| *C13B 30/02* | (2011.01) |

(52) U.S. Cl. ............. 127/41; 127/42; 127/46.1; 127/47; 127/50; 127/51; 127/53; 127/55; 127/56; 127/58; 127/61; 127/62

(58) Field of Classification Search ........................ None
See application file for complete search history.

(56) References Cited

U.S. PATENT DOCUMENTS

| | | | |
|---|---|---|---|
| 3,708,397 | A | 1/1973 | Sipos |
| 4,276,379 | A | 6/1981 | Heady |
| 4,710,231 | A | 12/1987 | Bateman et al. |
| 6,406,548 | B1 | 6/2002 | Donovan et al. |
| 6,916,381 | B2 | 7/2005 | Granguillhome et al. |

FOREIGN PATENT DOCUMENTS

| | | |
|---|---|---|
| ES | 2 136 553 | 11/1999 |
| FR | 2 073 697 | 10/1971 |
| GB | 949293 | 2/1964 |
| GB | 2 172 288 | 9/1986 |
| SU | 583137 | 12/1977 |
| WO | 03/016577 | 2/2003 |

OTHER PUBLICATIONS

International Search Report dated Feb. 10, 2008, from corresponding PCT application.

*Primary Examiner* — Emily Le
*Assistant Examiner* — Sarah A Slifka
(74) *Attorney, Agent, or Firm* — Young & Thompson

(57) ABSTRACT

A method for preparing a sugar syrup having high fructose content, is implemented using at least one fruit containing sorbitol, particularly apples, pears, plums, prunes, peaches, nectarines, apricots and grapes, from which a first juice is extracted. The first juice is processed in order to obtain a clarified and demineralised sweet juice having a colour lower than 45 ICUMSA and having a conductometric ash content lower than 0.4%. The clarified and demineralised sweet juice is then processed in order to hydrolyse the saccharose into fructose and glucose. The method further includes an isomerisation of the glucose in fructose, and removing the sorbitol naturally occurring in the starting material.

14 Claims, 2 Drawing Sheets

Figure 1:
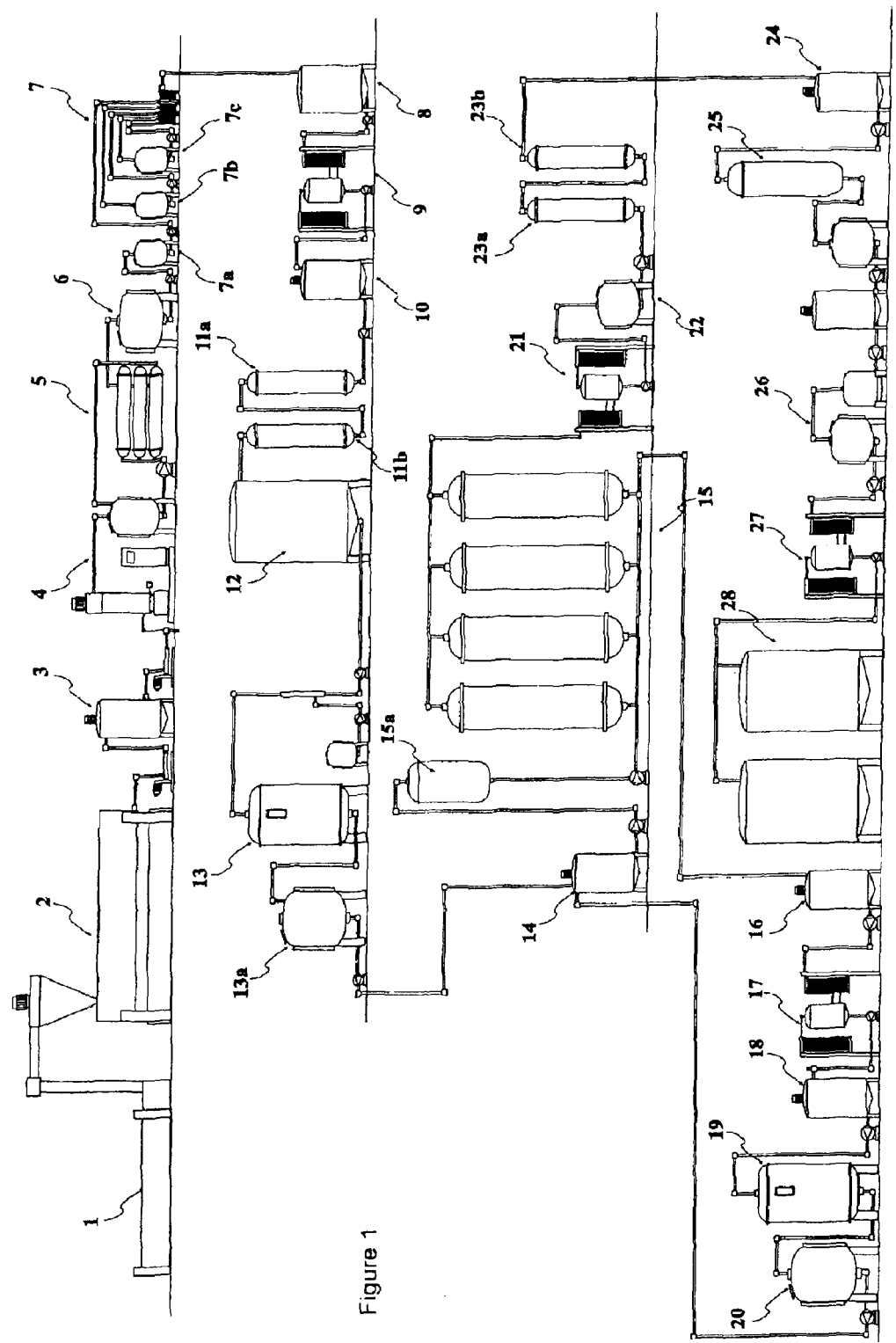

METHOD AND EQUIPMENT FOR PRODUCING FRUIT SUGAR SYRUPS HAVING HIGH FRUCTOSE CONTENT

The invention relates to the field of high-fructose sugar syrups. It relates more particularly to a method and installation for producing high-fructose sugar syrups from fruit.

Valued for its organoleptic properties (fruit flavours, feeling of coolness in the mouth) and its dietary properties (sweetening power 1.5 times that of sucrose, low rate of intestinal absorption, non-insulin-dependent metabolisation, low glycaemic index), fructose is currently of great interest in industry. Its consumption is no longer restricted to that of fruit, as it is now widely associated with the consumption of many processed products manufactured by the agri-food industry (sweeteners, sweetened drinks, jams, ice creams, confectionery, etc.).

On an industrial scale the production of fructose involves the use of an enzyme having glucose isomerase activity (FR 2 073 697) which allows glucose to be converted into fructose. In this context and to date, two main types of plant raw materials have been proposed as a source of glucose:

starch-rich plants (substantially corn, wheat, potatoes, etc.), from which starch is extracted and hydrolysed into glucose; this glucose is then converted into fructose;

sacchariferous plants (substantially sugar cane, sugar beet), from which a juice is extracted and then processed (for example by the method described in U.S. Pat. No. 6,406,548) to obtain a clarified and demineralised sweet sucrose juice; this sucrose is then hydrolysed to form a composition of simple sugars, glucose and fructose (for example by the method described in U.S. Pat. No. 6,916,381); the glucose is purified and then converted into fructose, augmenting the initial fructose fraction.

The production of concentrated fructose compositions by hydrolysis of inulin (a fructose polysaccharide) collected from chicory roots, dahlia bulbs and Jerusalem artichoke tubers has likewise been proposed.

The object of the invention is to propose a method for producing high-fructose sugar syrups which can be implemented using starting products other than sacchariferous plants, starch-rich plants and/or inulin-rich plants.

Throughout this document the expression "high-fructose sugar syrup" is used to describe a high-sugar composition containing at least 95% fructose relative to the total weight of dry matter, and/or at least 98% fructose relative to the total weight of sugars. For the sake of simplicity, the expression "fructose syrup according to the invention" can also be used to describe such a sugar syrup.

The invention provides a method intended for use on an industrial scale which by virtue in particular of its mode of operation, the choice of starting material and the quality of the end product is able to compete with traditional methods for producing "fructose syrups".

The invention also provides an industrial installation for the implementation of such a method.

The invention therefore relates to a method for producing a high-fructose sugar syrup wherein:
  a clarified and demineralised sweet juice is prepared from at least one initial plant raw material,
  said clarified and demineralised sweet juice is processed in order to hydrolyse the sucrose into fructose and glucose; a composition of simple sugars is then obtained containing a fructose fraction, referred to as the first fructose fraction, and a glucose fraction,
  the glucose fraction is separated from the first fructose fraction and the glucose contained in this glucose fraction is isomerised into fructose to form a new fructose fraction referred to as the second fructose fraction,
  the first and second fructose fractions are combined and are concentrated into a high-fructose sugar syrup.

A method for production according to the invention is characterised in that:
  1) at least one initial plant raw material is obtained from at least one fruit naturally containing sorbitol,
  2) an at least partial sorbitol elimination stage is included.

Said plant material is advantageously obtained according to the invention from at least one fruit selected from: apples, pears, plums, prunes, peaches, nectarines, apricots, grapes. In other words, a method for producing a sugar syrup having a high fructose content according to the invention is characterised in that it is performed using at least one fruit selected from: apples, pears, plums, prunes, peaches, nectarines, apricots, grapes.

According to the invention a first juice is advantageously extracted from said plant material and processed to obtain a clarified and demineralised sweet juice having a colour lower than 45 ICUMSA and having a conductometric ash content lower than 0.4%. This first juice can be obtained by any method of extracting juice from fruits—in particular by grinding and filtration and/or by pressing—from one or more fruits. This first juice can likewise consist of a mixture of several fruit juices, each obtained by extracting fruit juice from one or more fruits.

A method according to the invention is also characterised in that it likewise includes an at least partial sorbitol elimination stage. This sorbitol is naturally present in at least one fruit included in the composition of the initial plant raw material.

The invention thus relates to a method for producing sugar syrups having a high fructose content which is specifically suitable for the processing of fruits in which sorbitol is naturally present, such as apples, pears, plums, prunes, peaches, nectarines, apricots, grapes. As well as being among the most widely grown fruits in Europe, and particularly in France, the fruits at which the invention is directed experience a high wastage rate each year. The invention advantageously opens up a new industrial processing route for these fruits.

A method according to the invention is of the type involving a stage to separate a glucose fraction and a fructose fraction after hydrolysis of the sucrose, and a stage to convert the glucose into fructose; such is the case with the production of fructose syrups hitherto performed using sacchariferous plants.

In this respect it should be noted that the physico-chemical properties and the composition of fruits at which the invention is directed (apples, pears, plums, prunes, peaches, nectarines, apricots, grapes), which are very different from those of sacchariferous plants, do not allow the extraction and processing methods hitherto used with sacchariferous plants to be applied to such raw materials in their natural state, thus rendering these fruits apparently unsuitable for such a use.

In particular, in a method according to the invention, the operating parameters for the stages of extraction of the first juice and processing of this first juice to obtain a decolourised and demineralised sweet juice are accurately determined so as to enable sugars to be recovered from the fruits quickly and easily: fructose, but also sucrose and glucose, which are likewise naturally contained in these fruits.

The stages of clarification and demineralisation of the first juice (raw juice drawn directly from the starting material) are likewise performed in a method according to the invention in accordance with very particular purification principles and implementation parameters, specifically determined to lead precisely to a clarified and demineralised sweet juice having a colour lower than 45 ICUMSA and having a conductometric ash content lower than 0.4%.

The inventors have found that obtaining such a decolourised and demineralised sweet juice has a significant bearing on the success of the subsequent stages, and in particular:
- production of a composition of simple sugars by hydrolysis of the sucrose contained in the decolourised and demineralised sweet juice,
- separation of the glucose and fructose and elimination of the sorbitol,
- isomerisation of the glucose into fructose, and finally the obtaining of a high-quality fructose syrup.

According to the invention the first juice is advantageously put through the following processing stages in order to obtain a clarified and demineralised sweet juice:
- centrifugation in the order of 5000 to 14000 g,
- ultrafiltration through a porous membrane having a cut-off of between 1 kDa and 50 kDa,
- electrodialysis; the operating parameters are selected so as to allow at least partial elimination of the ionic charges from said first juice;
- chromatography on an anion-exchange resin and chromatography on a cation-exchange resin.

The stages for producing said clarified and demineralised sweet juice are performed in this sequence. This does not exclude the possibility of interruptions (during the course of these production stages and/or between two consecutive stages) and/or of additional stages introduced between these various stages.

The operating parameters for the centrifugation and ultrafiltration stages of a method according to the invention are chosen in particular to allow at least partial elimination of particles in suspension in the first juice and to obtain a clarified juice having an optical density, measured at 650 nm, of less than 0.10 U. To this end and according to the invention centrifugation is advantageously performed at 5000 g and ultrafiltration is advantageously performed with an ultrafiltration membrane having a cut-off in the region of 2.5 kDa and with application of a trans-membrane pressure in the region of 7 bar.

According to a particular embodiment of the invention, in order to produce the decolourised and demineralised sweet juice the first juice is subjected to the action of at least one enzyme having pectolytic activity prior to centrifugation. The enzymes developed specifically for the wine and/or fruit juice industry for sludge removal and/or clarification stages can advantageously be used for this purpose.

The operating parameters for the ultrafiltration and chromatography stages of a method according to the invention are likewise chosen specifically in order to obtain a demineralised juice having a conductometric ash content lower than 0.4%. To this end electrodialysis is advantageously performed according to the invention with operating parameters chosen so as to obtain a liquid composition having a conductivity at 50° C. of less than 800 µS·cm$^{-1}$. By way of example of the implementation, CMXsb cationic membranes (MITSUBISHI) and AXE01 and/or ASW anionic membranes (MITSUBISHI) are advantageously used. The voltage applied between the membranes is in the region of 14 V.

With regard to the chromatography stages on ion-exchange resins, cation-exchange chromatography is advantageously performed with a strong cationic resin and anion-exchange chromatography is advantageously performed with a weak anionic resin, optionally combined with a strong anionic resin.

Cationic or anionic resins are conventionally described as strong or weak according to their ionising capacity. Strong cationic resins are very highly ionised, regardless of their pH; in particular they are resins having sulfonic groups. Weak cationic resins for their part are no longer ionised in a highly acidic medium; in particular they are resins having carboxyl groups and resins having carboxymethyl groups. The most widely used strong anionic resins are the resins having quaternary amine groups and those having tertiary amine groups. The most widely used weak anionic resins are the resins having primary and secondary amine groups.

According to the invention the chromatography stages on ion-exchange resins are performed by choosing suitable operating parameters so as to obtain a decolourised and demineralised sweet juice having a conductometric ash content lower than 0.4%, preferably lower than 0.2%.

The conductometric ash content (which is substantially linked to the content of mineral salts, inorganic matter and organic acids) is traditionally determined by conductometry (i.e. by measuring electric conductivity) on a 28° B sugar solution at 20° C. A conductivity of 3.13 µS/cm corresponds to a conductometric ash content of 0.0018%.

According to the invention the decolourised and demineralised sweet juice obtained should then undergo hydrolysis of the sucrose. To this end an enzymatic hydrolysis is performed using an enzyme having β-D-fructofuranosidase activity (commonly known as invertase). This enzyme is advantageously used according to the invention in its immobilised form.

Once the sucrose has been hydrolysed, a composition of simple sugars is recovered which is principally composed of glucose and fructose, the glucose being intended for conversion to fructose. An enzyme having glucose isomerase activity in immobilised form is advantageously used to convert the glucose into fructose.

However, a composition of simple sugars prepared in accordance with the invention also contains a non-negligible amount of sorbitol. This sorbitol, which derives from at least one fruit in the initial plant raw material and which is found both in a decolourised and demineralised sweet juice and in a composition of simple sugars produced in accordance with the invention, has to be at least partially eliminated during the performance of the method according to the invention.

In this context the inventors found that this at least partial elimination of sorbitol could be performed by means of elution chromatography. What is more, this elimination was able to be performed quickly and easily by means of selective elution chromatography between fructose and sorbitol. To this end, and according to a preferred embodiment of the method according to the invention, the composition of simple sugars is processed by means of purification and isomerisation stages as described below.

The composition of simple sugars is subjected to elution chromatography on a $Ca^{2+}$ cationic resin column suitable for glucose-fructose separation. A fructose fraction and a glucose fraction are then obtained. Sorbitol is divided between these two fractions. This fructose fraction corresponds to the first fructose fraction within the meaning of the invention.

The glucose fraction obtained in this way is then subjected to isomerisation of the glucose into fructose. Elution chromatography is then performed on a $Ca^{2+}$ cationic resin column suitable for glucose-fructose separation. A new fructose fraction is recovered which corresponds to the second fructose fraction within the meaning of the invention.

Said first and second fructose fractions are combined to form a new fructose fraction. This new fructose fraction is subjected to elution chromatography on a $Ca^{2+}$ cationic resin column suitable for fructose-sorbitol separation. Suitable operating parameters are chosen so as to obtain a final fructose fraction having a sorbitol content of less than or equal to 5% relative to the total weight of dry matter (in the fraction).

According to this preferred embodiment of the invention the elution chromatography stages are advantageously performed using a $Ca^{2+}$ cationic resin column comprising two alternately operating outlet valves which is suitable for performing either glucose-fructose separation or fructose-sorbitol separation as required.

According to the invention an AMBERLITE CR 1320 $Ca^{2+}$ resin (ROHM AND HAAS, France) is advantageously used for the implementation of an elution chromatography column according to the invention.

According to the invention, in order to obtain a sugar syrup having a high fructose content in accordance with the invention said final fructose fraction is subjected to a final treatment for the purposes of demineralisation, deodorisation, decolourisation and elimination of any patulin which may be present, and to improve its long-term stability. To this end and according to the invention said final fructose fraction advantageously undergoes:

demineralisation by chromatography on ion-exchange resins,
activated carbon treatment,
a concentration stage.

According to the invention said demineralisation is advantageously performed on a mixed bed of two resins: a highly acidic cation-exchange resin and a highly alkaline anion-exchange resin. Suitable operating parameters are chosen so as to obtain a composition having a conductometric ash content lower than 0.2%, preferably lower than 0.1%.

According to the invention the activated carbon treatment is advantageously performed at a temperature in the region of 60° C. This activated carbon treatment serves to eliminate any patulin (a mycotoxin) which may be present and to eliminate residual colour and amine odours; these odours derive from the use of chromatography resins. According to the invention this activated carbon treatment is advantageously followed by filtration to trap the carbon particles entrained from the column. A sterilising filter is advantageously used for this purpose.

According to the invention the final fructose fraction is advantageously concentrated by means of a low-temperature vacuum evaporation process until a high-fructose sugar syrup is obtained having a sugar concentration in the region of at least 70% relative to the total weight of the composition (wet composition).

According to a preferred embodiment of a method according to the invention, in order to avoid the risk of contamination which can arise during production of the fructose syrup, concentration is performed until a sugar concentration is obtained in the region of at least 60% relative to the total weight of the composition on at least one sugar composition selected from: said decolourised and demineralised sweet juice, said composition of simple sugars, one of said fructose fractions, said glucose fraction. According to the invention a low-temperature vacuum evaporation process is advantageously used.

The method according to the invention allows a sugar syrup having a high fructose content to be obtained, referred to as the fructose syrup according to the invention. A fructose syrup according to the invention differs from fructose syrups produced by prior methods of extraction from plant raw material other than fruits by the presence of sorbitol, at least in trace form. This presence of sorbitol shows that a fruit has been used as the raw material for production of the syrup and serves to identify a fructose syrup according to the invention. This identification can be performed by HPLC analysis, for example.

In particular, a fructose syrup according to the invention has a fructose content of at least 95% relative to the total weight of dry matter and/or at least 98% relative to the total weight of sugars. A fructose syrup according to the invention likewise has a sorbitol content of less than or equal to 5% relative to the total weight of dry matter.

According to the invention a fructose syrup according to the invention advantageously has a sugar concentration in the region of at least 70%, relative to the total weight of the composition.

The invention likewise relates to an installation for the implementation of a method for producing a fructose syrup according to the invention. According to a preferred embodiment of an installation according to the invention, it comprises:

suitable means of extraction for extracting a first juice from at least one initial plant raw material obtained from at least one fruit naturally containing sorbitol—in particular chosen from apples, pears, plums, prunes, peaches, nectarines, apricots, grapes, refining equipment for producing from said first juice a decolourised and demineralised sweet juice having a colour lower than 45 ICUMSA and having a conductometric ash content lower than 0.4%, preferably lower than 0.2%, a reactor comprising an enzyme having β-D-fructofuranosidase activity, advantageously immobilised, which is suitable for hydrolysing the sucrose contained in the decolourised and demineralised sweet juice and for obtaining a composition of simple sugars, means of separating a fructose fraction and a glucose fraction starting from the composition of simple sugars, a reactor comprising an enzyme having glucose isomerase activity, advantageously immobilised, which is suitable for converting glucose into fructose, means of eliminating sorbitol.

According to the invention said refining equipment advantageously includes:
a centrifugation device,
an ultrafiltration column fitted with a porous membrane having a cut-off of between 1 kDa and 50 kDa, for example 2.5 kDa,
an electrodialyser capable of working with operating parameters suitable for obtaining a liquid composition having a conductivity of less than 800 $\mu S \cdot cm^{-1}$ at 50° C.,
an anion-exchange chromatography column (advantageously including a weak anionic resin) and a cation-exchange chromatography column (advantageously including a strong cationic resin).

According to the invention said installation advantageously includes an elution chromatography column having a $Ca^{2+}$ cationic resin (for example an AMBERLITE CR 1320 $Ca^{2+}$ resin from ROHM AND HAAS, France) and having two alternately operating outlet valves, suitable for performing either glucose-fructose separation or fructose-sorbitol separation as required.

According to the invention said installation advantageously includes suitable equipment for performing a final treatment of a fructose composition comprising demineralisation, deodorisation, decolourisation, elimination of any patulin that may be present, and concentration. To this end said equipment includes:

a chromatography column having a mixed bed of two resins: a highly acidic cation-exchange resin and a highly alkaline anion-exchange resin, an activated carbon column, the outlet from which is connected to a filtration device, a low-temperature vacuum evaporator.

The invention likewise relates to a method and an installation for producing a fructose syrup according to the invention, together characterised by some or all of the characteristics mentioned above or below.

Figure 2:
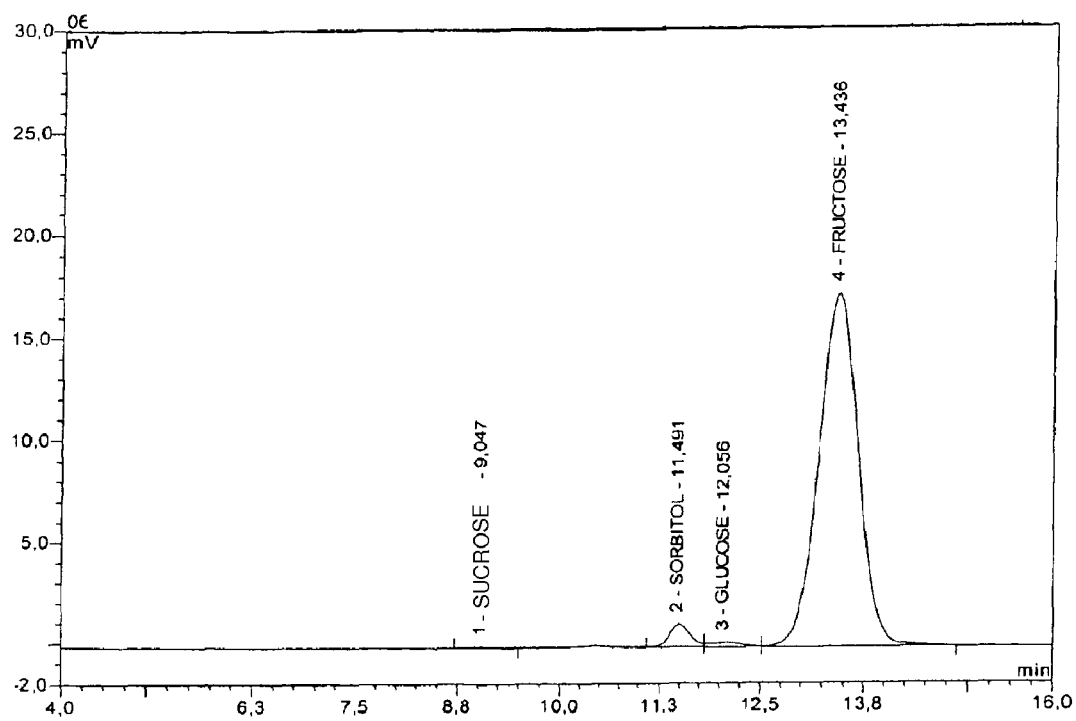

Other objects, characteristics and advantages of the invention will follow from reading the examples below and the description referring to the appended figures, which are not intended to be limiting. In the figures:

FIG. 1 is a schematic illustration of a specific example of an installation for producing a fructose syrup according to a preferred, but non-limiting, embodiment of a method according to the invention, FIG. 2 is an HPLC spectrum of a sugar syrup having a high fructose content obtained from apples, which has undergone a conversion process in accordance with the invention.

The description below relates to a particularly preferred embodiment of the method according to the invention.

The fruits, loaded onto a hydraulic conveyor 1, are washed and conveyed inside a device for extraction by grinding and filtration 2. A first juice is obtained at the exit.

Said first juice is collected in a first storage vessel 3 before being transferred into a centrifugation device 4 in order to obtain a clarified juice having an optical density (OD) measured at 650 nm of less than 0.1 U.

A pilot installation was constructed with a continuous vertical-bowl (tubular) centrifuge having a volume of 6.3 litres (model: SHARPLES AS 16) and operating with the following parameters:

an acceleration of 5000 g, a residence time of 10 minutes, with a processing capacity of around 6 m$^3$ per hour, an operating temperature in the region of 20° C.

Under these conditions OD reductions of over 90% were able to be obtained (values obtained in a test performed on apple juice):

94% for a suspension having an initial OD of 1.5 U (final OD 0.09 U)

91% for a suspension having an initial OD of 1.5 U (final OD 0.09 U)

96% for a suspension having an initial OD of 1.5 U (final OD 0.06 U).

In vessel 3, prior to the centrifugation stage, it is possible to perform a pre-clarification by addition of an enzyme having pectolytic activity. In such a case, after centrifugation under the operating conditions defined above, a supernatant is obtained having an OD of close to 0.05 U, measured at 650 nm.

The centrifuged and clarified fruit juice then passes through a series of ultrafiltration columns 5 fitted with polyether sulfone ultrafiltration membranes with a cut-off of 2.5 kDa.

At the exit from this ultrafiltration stage a decolourised filtrate is recovered in a vessel 6.

When the ultrafiltration rate drops, the residue is washed in order to minimise sugar losses.

In the pilot installation ultrafiltration is performed using a TIA ultrafiltration column (France) fitted with thin-film ultrafiltration membranes having a surface area of 1.77 m$^2$.

The operating pressures to which these membranes are exposed vary from 4.6 to 26 bar, with a maximum temperature of 50° C.

100 litres of apple juice were able to be processed in each test with this pilot plant. An average decolourisation rate of 90% was obtained using the following operating parameters:

recirculating pump: capacity 900 l/h trans-membrane pressure (TMP): 7 bar filtrate capacity: 5.6 l/h per m$^2$ of membrane surface area (this capacity falls steadily during processing, with a drop in capacity of around 3.5% of the initial capacity every 10 litres).

The fruit juice then passes through an electrodialyser 7 to reduce the concentration of salts and organic acids initially present in the fruit juice.

Electrodialysis is a separation method for use with ionic solutions. It uses an electric field which generates a motive force for the migration of ions in solution and ion-permeable membranes which ensure the selectivity of the ion migration and which also allow part of the ionic charge of the solutions to be removed.

In the pilot installation an AQUALYSEUR P1 electrodialyser from EIVS (France) was used and tested with two sets of membranes:

a stack of twenty electrodialysis cells, each comprising a cationic membrane, two separating frames and an anionic membrane; the complete set of cells has a total effective surface area of respectively 0.138 m$^2$ and 0.276 m$^2$ of the membrane (SELEMION AMV and CMV cells, from ASAHI GLASS CORPORATION, Japan), a EURB-10 stack provided by EURODIA (France); the ten active cells consist of twenty-two CMX sb cationic membranes and ten AXE 01 anionic membranes (NEOSEPTA-TOKUYAMA CORPORATION, Japan); the total active surface area of this stack is 0.2 m$^2$; with regard to the electrodes, the anode is made from TiPt, the cathode from stainless steel.

The electrodialyser consists of:

three vessels: the first, 7a, contains the juice for desalination, the second, 7b, contains the electrolyte, and the third, 7c, contains the brine recovered from the desalination stage;

three pumps (with polypropylene magnetic drive heads) having a recirculation capacity of up to 400 l.h$^{-1}$;

ball valves for recovering the processed products and regulating their flow rate.

This stage is used for a pre-demineralisation which extracts some of the organic acids and associated cations. Elimination of the organic acids and associated cations reduces the conductivity of the medium. This reduction in conductivity was monitored over time. The desalination rate varies between 50 and 97%, depending on the initial salt content and the processing time. The processing time is around ten minutes in the case of apple juice, for example.

The sugar concentration of the solutions for demineralisation by electrodialysis can vary between 12 and 50%, relative to the total weight of the solutions.

At the exit from the electrodialyser 7, the sweet juice generally has a sugar concentration of between 12 and 50%, relative to the total weight of juice, and a temperature of around 40° C. To avoid the risk of contamination of the diluted syrups, pre-concentration is provided at this stage. This is performed under vacuum at low temperature until a sugar concentration of around 60% is obtained, relative to the total weight of the composition.

To this end the sweet juice discharged from the electrodialyser 7 is collected in a vessel 8 and then sent to a vacuum evaporator 9. The concentrated product is transferred to the storage vessel 10.

Decolourisation and demineralisation are completed by means of ion-exchange chromatography, performed on two separate resin beds. To this end the pre-decolourised and pre-demineralised juice is passed through a first column 11a with a strong cationic resin, then through a second column 11b with a weak anionic resin.

Pilot tests were performed with double-walled glass columns from NORMARVER (France) supplied by means of Masterflex® peristaltic pumps. The first column contains 80 ml of Amberlite™ FPC22H, a strong cationic resin. The second column contains 80 ml of Amberlite™ FPA51, a weak anionic resin.

Before being used for the first time, these resins were passivated by being saturated three times in $MgSO_4$ and then regenerated.

To facilitate the flow at the top of the column, a layer of inert resin (Amberlite™ RF14) was added above the ion-exchange resins.

The sugar concentration of the solutions for demineralisation can vary between 12 and 50%, relative to the total weight of the composition.

The duration of the production phase in a cycle is dependent on the rate of pre-demineralisation. The supply flow applied is 5.5 $BV.h^{-1}$ (volume of product passing through the column per volume of substrate bed, per hour), corresponding to a flow rate of 440 $ml.h^{-1}$.

The decolourisation-demineralisation phase can be considered to be complete when the conductometric ash content at the exit from the anionic column is less than 0.4%, preferably less than 0.1%.

The cationic resin and the anionic resin are regenerated with quantities of pure HCl and NaOH respectively of 0.1 kg per litre of resin. The amount of water required for regeneration is 20 litres for a 2-litre pilot plant.

The decolourised and demineralised sweet juice obtained at the end of this first phase is recovered in a vessel 12 prior to undergoing sucrose hydrolysis. This concentrated sweet juice principally consists of a mixture of sucrose, fructose and glucose, along with some sorbitol.

Hydrolysis of the sucrose takes place in a continuous fixed-bed reactor 13 containing the β-D fructofuranosidase in immobilised form. The reactor 13 is supplied in a downward flow.

Before being transferred into the reactor 13 the decolourised and demineralised sweet juice passes through a buffer vessel, inside which its pH is adjusted to the optimum pH for catalysis of the enzyme used, in this case 4.5 for a temperature of around 30° C.

The initial supply flow of the reactor 13 can vary between 0.3 and 1 $BV.h^{-1}$, depending on the initial sucrose content of the decolourised and demineralised sweet juice. During the course of the reaction the loss of activity of the enzyme is offset by increasing the temperature in order to maintain a sucrose hydrolysis rate greater than or equal to 99%. The temperature variation increment is 1° C., up to 60° C. The composition of simple sugars obtained at this stage is referred to as "fruit invert" in the examples below.

The composition of simple sugars produced by this hydrolysis substantially contains glucose and fructose (possibly traces of sucrose) and a non-negligible amount of sorbitol (highly variable from one fruit to another and from one variety of fruit to another). It is routed to a vessel 13a.

Depending on the variety of fruit, it is possible to obtain compositions of simple sugars having sorbitol contents well above 6%, relative to the total weight of dry matter.

The composition of simple sugars is collected in a vessel 14 and then passed through a series of elution chromatography columns 15 regulated so as to allow a glucose-fructose separation. The resin used is a $Ca^{2+}$ cationic resin. Separation is carried out using water purified by reverse osmosis. To prevent oxidation of the resins, the elution water and the supply solution must be degasified in a flash flask 15a.

At the exit from the chromatography columns a fructose fraction and a glucose-rich fraction are obtained. The sorbitol previously contained in the composition of simple sugars is divided between the fructose and glucose fractions.

With regard to the glucose fraction discharged from the chromatography columns 15 (following fructose-glucose separation chromatography), it is initially collected in a vessel 16. To limit the risk of contamination, this fraction is rapidly concentrated to a sugar concentration of around 60%, relative to the total weight of the composition, using a vacuum evaporator 17 operating at low temperature. The concentrated glucose fraction is recovered in a vessel 18.

The isomerisation stage from glucose to fructose is performed continuously in a fixed-bed reactor 19 containing a glucose isomerase in immobilised form. The reactor 19 is supplied in a downward flow.

Prior to isomerisation, the concentrated glucose fraction passes through a buffer vessel (not shown in the figure) where its pH is adjusted to 7 using a solution of ($K^+$, $OH^-$).

The concentrated glucose fraction, buffered and mixed with a solution of $MgCl_2$ (for a final concentration of 3 mM) is sent to the reactor 19 at a constant flow rate. At the exit from reactor 19, a syrup containing around 48% fructose and 52% glucose, relative to the total weight of dry matter, is recovered in a vessel 20.

The loss of activity of the enzyme is offset by a gradual rise in the temperature of reactor 19. The temperature variation increment in reactor 19 is 1° C. The temperature range of reactor 19 is fixed between 35° C. and 60° C.

To separate the glucose and the fructose in the syrup collected in vessel 20, this syrup is returned to the chromatography columns 15 via vessel 14, inside which it is mixed with the composition of simple sugars obtained from the stage of sucrose hydrolysis from the decolourised and demineralised sweet juice.

With regard to the fructose fractions discharged from the chromatography columns 15, they are circulated through these chromatography columns 15 again. When the fractions pass through the chromatography columns once more, the columns are adjusted to allow a fructose-sorbitol separation to take place.

In particular, the operating parameters for the columns 15 are adjusted so as to obtain a final fructose fraction having a sorbitol content of less than or equal to 5% relative to the total weight of dry matter in the composition.

This final fructose fraction, which has been largely freed from sorbitol, is first concentrated to a sugar concentration of around 60%, relative to the total weight of the fraction (wet fraction) using a vacuum evaporator 21 operating at low temperature and then collected in vessel 22.

Before it can be marketed, this fructose syrup goes through a series of final treatments for the purposes of demineralisation, deodorisation, decolourisation and elimination of any patulin which may be present, and to improve its long-term stability.

The fructose syrup is first decolourised and demineralised by chromatography on a mixed bed of resins produced by a mixture of two resins: a highly acidic cation-exchange resin and a highly alkaline anion-exchange resin.

Two chromatography columns 23a and 23b are used in series for this purpose. Once the first column 23a is saturated, it is regenerated. The entire flow then passes through the second column 23b. Following regeneration, the first column 23a is used in the second position and the flow again passes through the two columns in series.

When the composition leaves this mixed bed of resins its conductometric ash content is only around 0.2% or even lower.

The decolourised and demineralised fructose syrup is collected in a vessel 24.

In a second stage the fructose syrup undergoes activated carbon treatment to remove amine odours, the possible presence of patulin and residual coloration. The treatment is performed in column 25. The treatment temperature is 60° C.

A carbon trap 26 is provided at the exit from column 25.

The fructose syrup treated in this way is finally concentrated to a sugar concentration of around 70% relative to the total weight of the composition, using a vacuum evaporator 27 operating at low temperature.

The final fructose syrup, having a sugar concentration of around 70% relative to the total weight of the composition, is stored in tanks 28 pending packaging as a finished product, ready for consumption in its present state, and/or pending shipment to other agri-food industries for conversion.

Utilising some or all of the stages, the method according to the invention described above was used to obtain sugar syrups from apple juice (example 1), peach juice (example 2) and a mixture of melon and peach juice (example 3).

EXAMPLE 1

The method according to the invention for producing a fructose syrup according to the invention was performed using a pre-concentrated apple juice. The physico-chemical properties of the initial juice and of the syrup obtained are set out in Table 1 below:

TABLE 1

| Physico-chemical characteristics | Fructose syrup |
| --- | --- |
| Refractive index (° Brix) at 20° C. | 70 |
| pH (+/−1) at 30° Brix | 4.68 |
| Conductometric ash in g % g | 0.002 |
| Conductivity µS/cm at 28° B | 4 |
| Colour (ICUMSA) at 50° Brix | <2 |
| Fructose (% of total sugars) | 98.9% |
| Glucose (% of total sugars) | 0.9% |
| Sucrose (% of total sugars) | 0.2% |
| Sorbitol/total sugars in % | <4.5% |

FIG. 2 shows the HPLC spectrum for the apple sugar syrup obtained.

This syrup was analysed under the following operating conditions:
Column: BIORAD HPX87 K
Eluant: Ultrapure water
Flow rate: 0.6 ml.min$^{-1}$
Temperature: 65° C.

Table 2 below sets out the results of the analysis obtained.

TABLE 2

| Peak | Retention (min) | Compound | Proportion of surface area (%) | Concentration (g · l$^{-1}$) |
| --- | --- | --- | --- | --- |
| 1 | 9.05 | Sucrose | 0.23 | 0.018 |
| 2 | 11.49 | Sorbitol | 3.33 | 0.254 |
| 3 | 12.06 | Glucose | 0.93 | 0.072 |
| 4 | 13.44 | Fructose | 95.51 | 7.448 |
| Total: | | | 100.00 | 7.791 |

EXAMPLE 2

The method according to the invention for producing a fructose syrup according to the invention was performed using a peach juice. The physico-chemical properties of the initial juice and of the syrup obtained are set out in Table 3 below.

TABLE 3

| Physico-chemical characteristics | Fructose syrup |
| --- | --- |
| Refractive index (° Brix) at 20° C. | 70– |
| pH (+/−1) at 30° Brix | 4.5 +/− 0.5 |
| Colour (ICUMSA) at 50° Brix | <45 |
| Fructose (total sugars in %) | 98.8 |
| Glucose (total sugars in %) | 1.2 |
| Sucrose (total sugars in %) | 0.01 |
| Sorbitol/total sugars in % | <4.5% |

EXAMPLE 3

Based on examples 1 and 2, a fructose syrup composition having a fructose content of at least 95% relative to the total weight of dry matter and obtainable in accordance with the invention can be analysed by means of a calculation method which takes the various chromatography parameters into consideration.

The initial plant raw material can be obtained firstly from fruits containing sorbitol and secondly from fruits not containing sorbitol which are mixed with the former group.

Table 4 below sets out a non-exhaustive list of fruits which always contain sorbitol and fruits which may contain sorbitol, depending on their origin and/or variety. The total sugar concentrations (high value and low value) in these fruits along with the sorbitol concentrations (high value and low value) are likewise listed:

TABLE 4

| | Total sugars g % g of fruit | Sorbitol g % g of fruit | Average percentage of sorbitol/total sugars + sorbitol |
| --- | --- | --- | --- |
| Plum (2) | 8-18.6 | 7.4-8.6 | 37.4% |
| Pear (1) | 7.9-13.3 | 1.21-2.8 | 17.6% |
| Cherry (2) | 14.4 | 2.9 | 16.9% |
| Plum (1) | 5.2-13.2 | 2.0-0.6 | 16.0% |
| Cherry (1) | 11.9-24.8 | 1.4 | 7.7% |
| Nectarine | 7.3-8.6 | 0.6-0.7 | 7.6% |
| Apricot | 3.1-12.4 | 0.12-1.2 | 4.9% |
| Apple (1) | 9-14 | 0.2-1.0 | 4.7% |
| Peach | 8.9 | 0.4 | 4.5% |

The values listed in Table 5 are derived from analyses performed by the inventors by HPLC, and from the following publications:

(1) Free sugars sorbitol fruits compilation from literature (1981). R. E. Wrolstad, R. S. Shallenberger, JAOAC, 64, 91-103.

(2) Compositional Characterization of prune juice (1992). H. van Gorsel and coll., J. Agric. Food Chem., 40, 784-789.

Other juices obtained from plant raw material and not containing sorbitol can be used in combination with the fruit juices or concentrates described above, for example at least one juice selected from citrus juices, citrus molasses juices, kiwi juices and melon juices, said list not being exhaustive.

The composition of fructose syrups which can be obtained according to the invention was simulated from analyses performed on commercial fruit juices. Three examples are given in Tables 5 to 7 below: orange/prune juice (Table 5), kiwi/pear juice (Table 6) and nectarine/grape juice (Table 7). The chosen proportions correspond here to 50% of juice A to 50% of juice B, but they can vary from 1 to 99% and the combinations described are not limiting.

TABLE 5

| Physico-chemical characteristics | Fructose syrup |
|---|---|
| Refractive index (° Brix) at 20° C. | 70 +/− 2 |
| pH (+/−1) at 30° Brix | 4.5 +/− 0.5 |
| Conductometric ash in g % g | <0.1 g % g |
| Colour (ICUMSA) at 50° Brix | <45 |
| Fructose (% of total sugars) | 98.3 |
| Glucose (% of total sugars) | 1.7 |
| Sucrose (% of total sugars) | 0 |
| Sorbitol/total sugars | <4.5% |

TABLE 6

| Physico-chemical characteristics | Fructose syrup |
|---|---|
| Refractive index (° Brix) at 20° C. | 70 +/− 2 |
| pH (+/−1) at 30° Brix | 4.5 +/− 0.5 |
| Conductometric ash in g % g | <0.1 g % g |
| Colour (ICUMSA) at 50° Brix | <45 |
| Fructose (% of total sugars) | 97.9 |
| Glucose (% of total sugars) | 2.1 |
| Sucrose (% of total sugars) | 0 |
| Sorbitol/total sugars | <4.5% |

TABLE 7

| Physico-chemical characteristics | Fructose syrup |
|---|---|
| Refractive index (° Brix) at 20° C. | 70 +/− 2 |
| pH (+/−1) at 30° Brix | 4.5 +/− 0.5 |
| Conductometric ash in g % g | <0.1 g % g |
| Colour (ICUMSA) at 50° Brix | <45 |
| Fructose (% of total sugars) | 98.3 |
| Glucose (% of total sugars) | 1.7 |
| Sucrose (% of total sugars) | 0 |
| Sorbitol/total sugars (%) | <4.5% |

The invention claimed is:

1. A method for producing a sugar syrup having a high fructose content, comprising:
   preparing a clarified and demineralised sweet juice from at least one initial plant raw material,
   processing said clarified and demineralised sweet juice in order to hydrolyse the sucrose into fructose and glucose and obtaining a composition of simple sugars containing a first fructose fraction and a glucose fraction,
   separating the glucose fraction from the first fructose fraction and isomerizing glucose contained in the glucose fraction into fructose to form a second fructose fraction,
   combining the first and second fructose fractions and concentrating the combined fractions into a high-fructose sugar syrup,
   wherein in said method:
      the at least one initial plant raw material is obtained from at least one fruit naturally containing sorbitol, and
      the method includes a step of at least partially eliminating sorbitol.

2. The method as claimed in claim 1, wherein said plant material is obtained from at least one fruit selected from the group consisting of: apples, pears, plums, prunes, peaches, nectarines, apricots, and grapes.

3. The method as claimed in claim 1, wherein preparing the clarified and demineralised sweet juice comprises extracting a first juice from said plant material and processing the first juice to obtain a clarified and demineralised sweet juice having a colour lower than 45 ICUMSA and having a conductometric ash content lower than 0.4%.

4. The method as claimed in claim 3, wherein processing the first juice comprises conducting the following processing stages in order to obtain said clarified and demineralised sweet juice:
   centrifugation in a range of 5000 to 14000 g;
   ultrafiltration through a porous membrane having a cut-off of between 1 kpa and 50 kpa;
   electrodialysis with suitable operating parameters selected so as to allow at least partial elimination of ionic charges from said first juice;
   chromatography on an anion-exchange resin and on a cation-exchange resin.

5. The method as claimed in claim 4, wherein the electrodialysis is performed with operating parameters selected so as to obtain a liquid composition having a conductivity at 50° C. of less than 800 $\mu S.cm^{-1}$.

6. The method as claimed in claim 4, wherein said chromatography is performed with a strong cationic resin and with a weak anionic resin and with suitable operating parameters to obtain the clarified and demineralised sweet juice having a conductometric ash content lower than 0.4%.

7. The method as claimed in claim 1, wherein an enzyme having β-D-fructofuranosidase activity in immobilised form is used to hydrolyse the sucrose into sucrose and glucose.

8. The method as claimed claim 1, wherein an enzyme having glucose isomerase activity in immobilised form is used to isomerise the glucose into fructose.

9. The method as claimed in claim 1, comprising:
   subjecting said composition of simple sugars to elution chromatography on a $Ca^{2+}$ cationic resin column suitable for glucose-fructose separation and obtaining said first fructose fraction and said glucose fraction,
   subjecting the glucose fraction to isomerisation of glucose into fructose, then performing elution chromatography on a $Ca^{2+}$ cationic resin column suitable for glucose-fructose separation and recovering said second fructose fraction,
   combining said first and second fructose fractions to form a new fructose fraction and subjecting said new fructose fraction to elution chromatography on a $Ca^{2+}$ cationic resin column suitable for fructose-sorbitol separation, suitable operating parameters being chosen so as to obtain a final fructose fraction having a sorbitol content of less than or equal to 5%, relative to the total weight of dry matter in the final fructose fraction.

10. The method as claimed in claim 9, wherein the final fructose fraction is subjected to:
   demineralisation by chromatography on ion-exchange resins,
   activated carbon treatment, and
   a concentration stage.

11. The method as claimed in claim 10, wherein said demineralisation is performed with suitable operating parameters so as to obtain a composition having a conductometric ash content lower than 0.2%.

12. The method as claimed in claim 1, wherein to avoid a risk of contamination a concentration is performed until a sugar concentration is obtained in a region of at least 60% relative to the total weight of the composition on at least one sugar composition selected from: said decolourised and demineralised sweet juice, said composition of simple sugars, one of said fructose fractions, said glucose fraction.

13. The method as claimed in claim 1, wherein at least partially eliminating sorbitol comprises subjecting the combined first and second fructose fractions to elution chromatography on a $Ca^{2+}$ resin column suitable for fructose-sorbitol separation.

14. The method as claimed in claim 6, wherein said chromatography is performed on a mixed bed of cation-exchange resin and anion-exchange resin.

* * * * *